(12) United States Patent
Arai et al.

(10) Patent No.: US 6,335,982 B1
(45) Date of Patent: Jan. 1, 2002

(54) METHOD AND APPARATUS FOR INSPECTING STREAK

(75) Inventors: Noriyuki Arai; Mitsuo Komori, both of Kawasaki (JP)

(73) Assignee: Toshiba Engineering Corporation, Kawasaki (JP)

(*) Notice: Subject to any disclaimer, the term of this patent is extended or adjusted under 35 U.S.C. 154(b) by 0 days.

(21) Appl. No.: 09/481,524

(22) Filed: Jan. 12, 2000

Related U.S. Application Data

(63) Continuation-in-part of application No. 08/882,152, filed on Jun. 25, 1997.

(30) Foreign Application Priority Data

Jun. 26, 1996 (JP) .............................................. 8-165729

(51) Int. Cl.⁷ ................................................ G06K 9/00
(52) U.S. Cl. ...................................... 382/149; 356/600
(58) Field of Search ................................. 382/141, 143, 382/149, 303, 304; 356/237, 375, 376, 429, 390, 392, 394, 430, 431; 250/559.39, 559.41, 559.42, 559.43, 559.45, 559.46, 559.48, 559.29

(56) References Cited

U.S. PATENT DOCUMENTS 4,974,261 A * 11/1990 Nakahara et al. ........... 382/141
5,929,996 A * 7/1999 Itagaki et al. ............... 356/613
6,023,334 A * 2/2000 Itagaki et al. ............... 356/600

FOREIGN PATENT DOCUMENTS

EP 0 651 352 A1 * 5/1995

* cited by examiner

Primary Examiner—Samir Ahmed
(74) Attorney, Agent, or Firm—Oblon, Spivak, McClelland, Maier & Neustadt, P.C.

(57) ABSTRACT

A method and an apparatus for inspecting a streak on a sheet object to be inspected are provided. The apparatus includes a micro-filtering unit for enlarging a width of defect data and an unevenness filtering unit connected to the micro-filtering unit in series, for detecting the defect data having a certain measure of width. Inputting image data, which has been taken by a line sensor camera, through an image input unit, the micro-filtering unit outputs data of a microscopic streak with low contrast to the unevenness filtering unit while enlarging the width of the streak.

5 Claims, 11 Drawing Sheets

MICRO-FILTERING UNIT

VERTICAL SOBEL FILTER

31 →

| -1 | 0 | 1 |
|----|---|---|
| -2 | 0 | 2 |
| -1 | 0 | 1 |

FIG.6
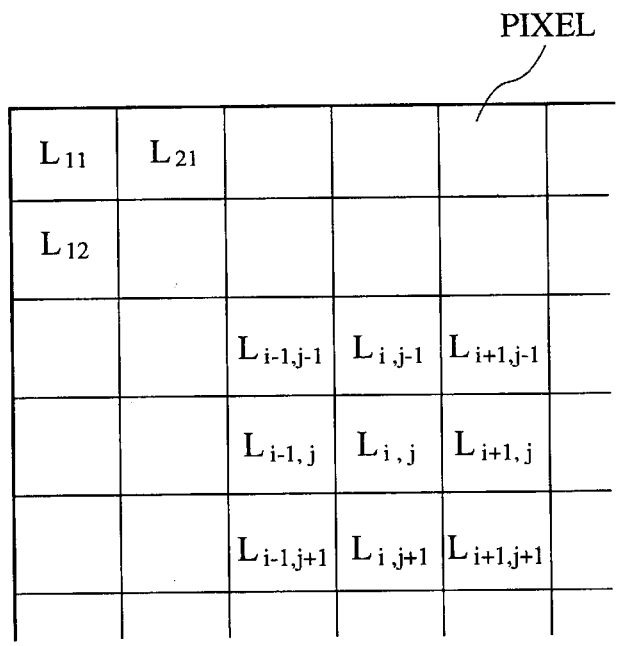
FIG.7A    FIG.7B
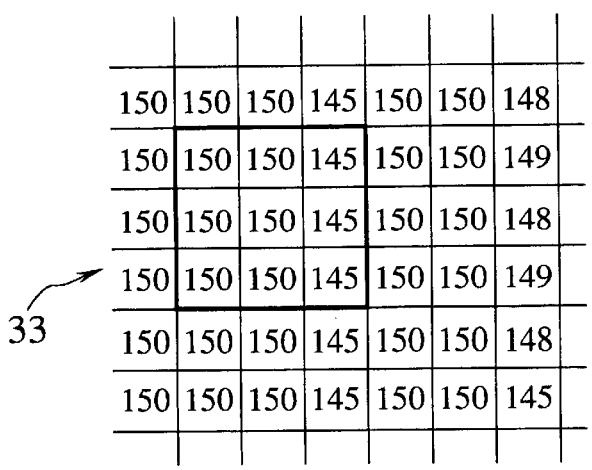
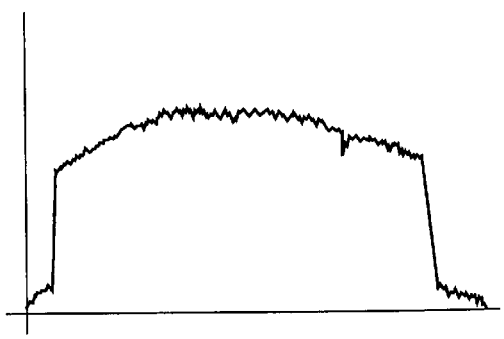

FIG.8A
| | | | | |
|---|---|---|---|---|
| 0 | -20 | 0 | 20 | 6 |
| 0 | -20 | 0 | 20 | 6 |
| 0 | -20 | 0 | 20 | 6 |
| 0 | -20 | 0 | 20 | 10 |
34
FIG.8B
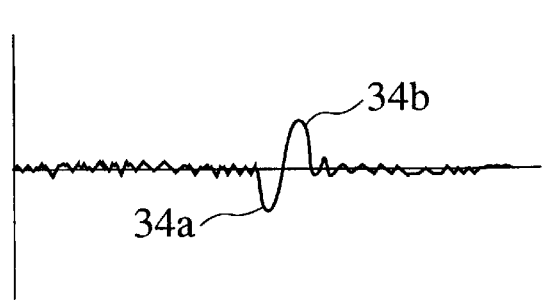
34b
34a
FIG.9A
| | | | | |
|---|---|---|---|---|
| 0 | 20 | 0 | 20 | 6 |
| 0 | 20 | 0 | 20 | 6 |
| 0 | 20 | 0 | 20 | 6 |
| 0 | 20 | 0 | 20 | 10 |
FIG.9B

$$\frac{n}{N} < \frac{s}{S}, W < w$$

UNEVENNESS-FILTERING UNIT

METHOD AND APPARATUS FOR INSPECTING STREAK

This application is a continuation-in-part of Ser. No. 08/882,152, filed Jun. 25, 1997, which is expressly incorporated by reference herein in its entirety.

BACKGROUND OF THE INVENTION

The present invention relates to a method of and an apparatus for inspecting a streak on a sheet product with ease, the streak being low in contrast, narrow in width and long in a direction along which the sheet product is to be transported.

For example, in the manufacturing line for producing sheet products, such as a paper, a film, a steel plate or the like, it is necessary to inspect whether the sheet product has surface defects formed thereon, such as lines, scratches, irregularities, dirty marks (blots), alien substances etc.

In order to inspect such surface defects, it is general to take respective pictures of the sheet product by means of a "line sensor" camera arranged above the materials on transportation. Then, video signals generated from the line sensor camera are processed for images in order to emphasize the defects.

As to this image processing, Japanese Unexamined Patent Publication (Kokai) No. 7-225196 discloses a method of detecting fine (microscopic) defects. In the method, the video signals from the line sensor camera are converted into digital image data and sequentially, the resultant digital image data is processed under micro-filtering for emphasizing the fine defects. Alternatively, Japanese Unexamined Patent Publication (Kokai) No. 6-323954 discloses a method for detecting light unevenness (e.g. patterns) or dark unevenness (e.g. blots ) In this method, the resultant digital image data is processed by using an unevenness filter, for emphasizing such an unevenness. That is, hitherto, different kinds of inspection methods have been employed in accordance with the kinds of defects to be inspected.

However, it should be noted that the above-mentioned micro-filtering process comprises a step of emphasizing changes in density information of respective pixels (i.e. picture elements) and a sequent step of averaging the respective changes. Then, when a difference between the averaged changes is more than a predetermined threshold value, it is judged that the inspected product contains a microscopic defect.

Thus, according to the judgement of the micro-filtering process, a difference of density value of one pixel is firstly emphasized and thereafter, when the difference is more than the predetermined value, the object to be inspected is judged to have a defect. Therefore, unless the object to be inspected has a certain extent of the difference of density, the surface defect, such as streaks, cannot be detected.

Since, for example, the above-mentioned streak etc. of low contrast, which is narrow in width and long in the transporting direction, has a small density, the resultant difference in density will be too small to exceed the threshold value. Thus, in this case, it is impossible to detect such a streak or the like.

Therefore, it has been concluded that in the micro-filtering process, it is impossible to detect any the defects exhibiting low contrast.

In the meanwhile, the unevenness filtering process comprises a step of dividing the image data as the density information of pixels into lattices consisting of designated number of pixel matrixes lengthwise and breadthwise, a sequent step of emphasizing its unevenness by integrating the density information of each pixel contained in the respective lattices and a further step of calculating a difference between the so-obtained integration value and the other integration value. Then, if the calculated difference is more than a predetermined value, it is judged that the product contains an unevenness as a defect.

That is to say, in the unevenness filtering process, respective densities of the plural pixels are firstly integrated and the difference between the integration values is defined as an unevenness. Therefore, unless a certain extent of area is ensured for inspection, it is impossible to detect such an unevenness, disadvantageously.

SUMMARY OF THE INVENTION

Under such a circumstance, it is therefore an object of the present invention to provide a streak inspection method and a streak inspecting apparatus, by which it is possible to detect the streaks with ease, no matter how low of contrast, narrow in width and long in the transporting direction they may be.

The object of the present invention described above can be accomplished by a streak inspection method of inspecting an existence of a streak on a sheet object to be inspected for defect data, the defect data obtained from pixel image data corresponding to a picture taken of the sheet during transportation, the streak inspection method comprising:

a first step of emphasizing changes in density information for each pixel forming the image data;

a second step of adding plural data emphasized at the first step;

a third step of calculating changes among the data added at the second step; and a fourth step of detecting the streak by comparing the changes calculated at the third step with a predetermined threshold value;

wherein the first step, the second step and the third step are performed in series.

Alternatively, it is also preferable that the first step comprises:

a step of enlarging a width of the defect data by averaging the emphasized changes in density information. The above-mentioned object can be accomplished by providing A streak inspection apparatus for inspecting an existence of a streak on a sheet object to be inspected for defect data, the defect data obtained from pixel image data corresponding to a picture taken of the sheet during transportation, the streak inspection apparatus comprising:

memory means for storing density information for each pixel forming the image data;

a first change calculating means for emphasizing plural changes in the density information for the each pixel forming the image data;

a second change calculating means for dividing the plural changes data into lattices in a manner that a number of data of the sheet object in a direction of the transportation is larger than a number of data of the sheet object in a direction perpendicular to the direction of the transportation and subsequently, calculating changes in density information in each one of the lattices; and comparing means for comparing the changes obtained by the second change calculating means with a predetermined threshold value;

wherein the first change calculating means is connected in series with the second change calculating means.

In the present invention, preferably, the first change calculating means comprises means for averaging the plural changes.

These and other objects and features of the present invention will become more fully apparent from the following description and appended claims taken in conjunction with the accompany drawing.

BRIEF DESCRIPTION OF THE DRAWINGS

FIG. 6 is an explanatory diagram for calculation of changes in the micro-filtering unit;

FIGS. 7A and 7B are explanatory diagrams of a process of calculating a sum of integral values in the micro-filtering unit;

FIGS. 8A and 8B are explanatory diagrams for explanation of a result of the process of calculating the sum of integral values in the micro-filtering unit;

FIGS. 9A and 9B are explanatory diagrams for explanation of a calculation result of the changes in the micro-filtering unit;

DESCRIPTION OF THE PREFERRED EMBODIMENT

An embodiment of the present invention will be described with reference to the drawings. U.S. Pat. No. 5,929,996, filed Nov. 5, 1996, Itagaki et al., is incorporated by reference herein in its entirety.

Figure 1:
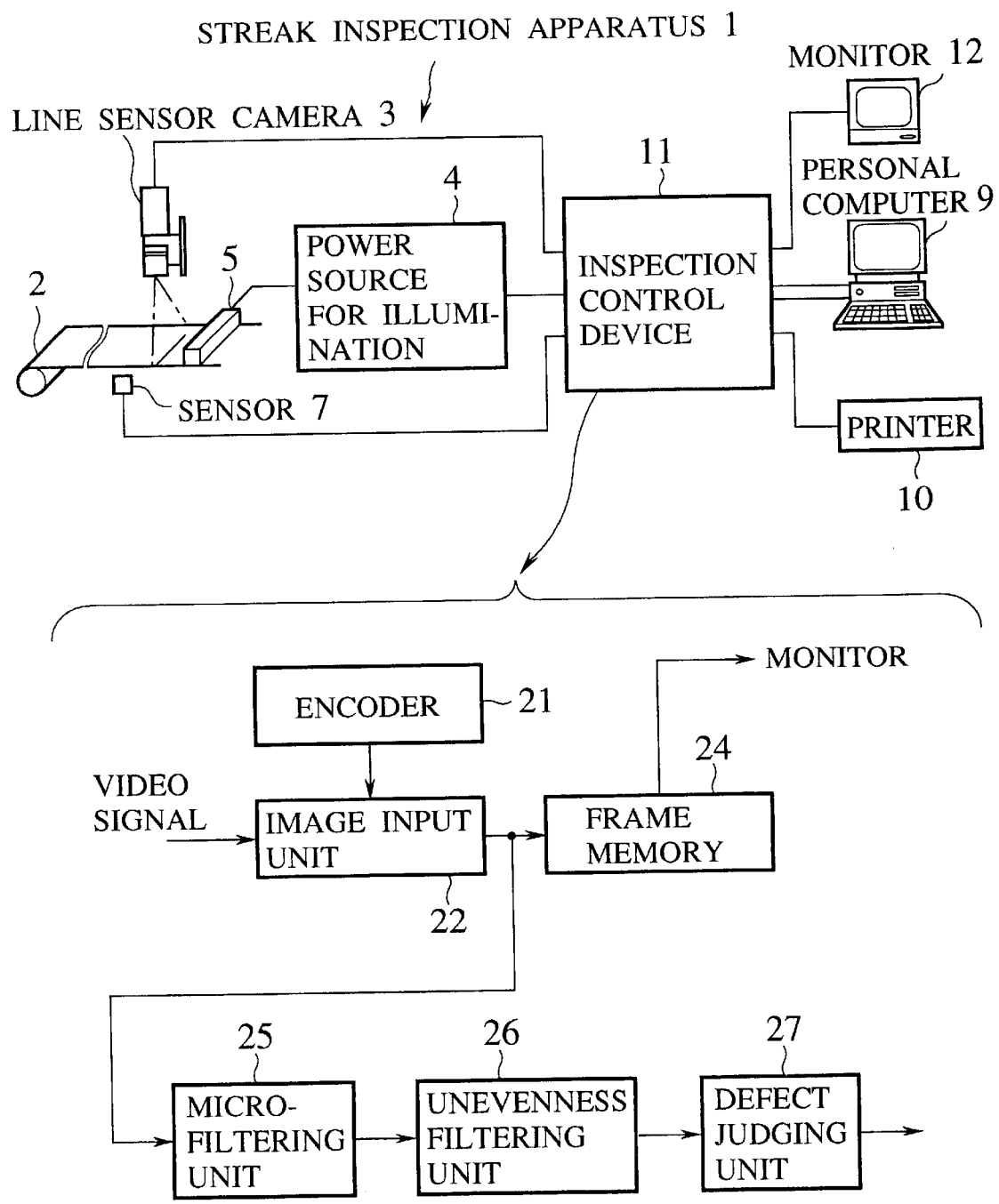
FIG. 1 is a schematic constituent diagram of a streak inspection apparatus in accordance with an embodiment of the present invention.

FIG. 1 is a schematic constituent diagram of a streak inspection apparatus in accordance with an embodiment of the present invention. The streak inspection apparatus 1 of FIG. 1 comprises a line sensor camera 3 for taking pictures of a surface of a sheet 2, an illuminator 5 arranged in the vicinity of an image pickup line that the line sensor camera 3 takes for irradiating light produced by electric power from an illumination power source 4, a sensor 7 positioned on the upper stream side of the line sensor camera 3 for detecting the sheet 2, and an inspection control device 11. When the sensor 7 detects the sheet 2, the inspection control device 11 operates to input picture signals from the line sensor camera 3 every stated lines in order to detect the streaks (including streaks having low contrast) from the image data corresponding to the lines taken in and subsequently outputs the inspection results to a personal computer 9 and a printer 10.

The inspection control device 11 is provided with a monitor 12 for displaying images of the sheet 2.

As shown in FIG. 1, the inspection control device 11 of the streak inspection apparatus 1 includes an encoder 21, an image input unit 22, a frame memory 24, a micro-filtering unit 25, an unevenness filtering unit 26, and a defect judging unit 27.

The encoder 21 outputs pulse signals to the image input unit 22 at regular intervals.

When the sensor 7 detects the sheet 2, the encoder 21 operates to output pulse signals to the image input unit 22, the pulse signals each of which has a width for resolving an image.

With an input of the pulse signals from the encoder 21, the image input unit 22 synchronizes video signals in every lines from the line sensor camera 3 with the pulse signals from the encoder 21 thereby to generate digital image data (density of pixels) constituting one line.

The micro-filtering unit 25 operates to emphasize the changes of density information of respective pixels, which have been brought from the image input unit 22, and subsequently averages the changes. Consequently, the micro-filtering unit 25 outputs image data in which defects (e.g. microscopic irregularities, profiles of pinholes etc.) are emphasized.

Dividing the image data as the density information of pixels into lattices consisting of a designated number of pixel matrixes lengthwise and breadthwise, the unevenness filtering unit 26 operates to emphasize the unevenness by integrating the density information of the respective pixels of each lattice.

If the unevenness emphasized in the unevenness filtering unit 26 has a designated length, the defect judging unit 27 judges it to be a streak.

In addition, the defect judging unit 27 outputs the inspection results to the personal computer 9 or the printer 10.

Figure 2:
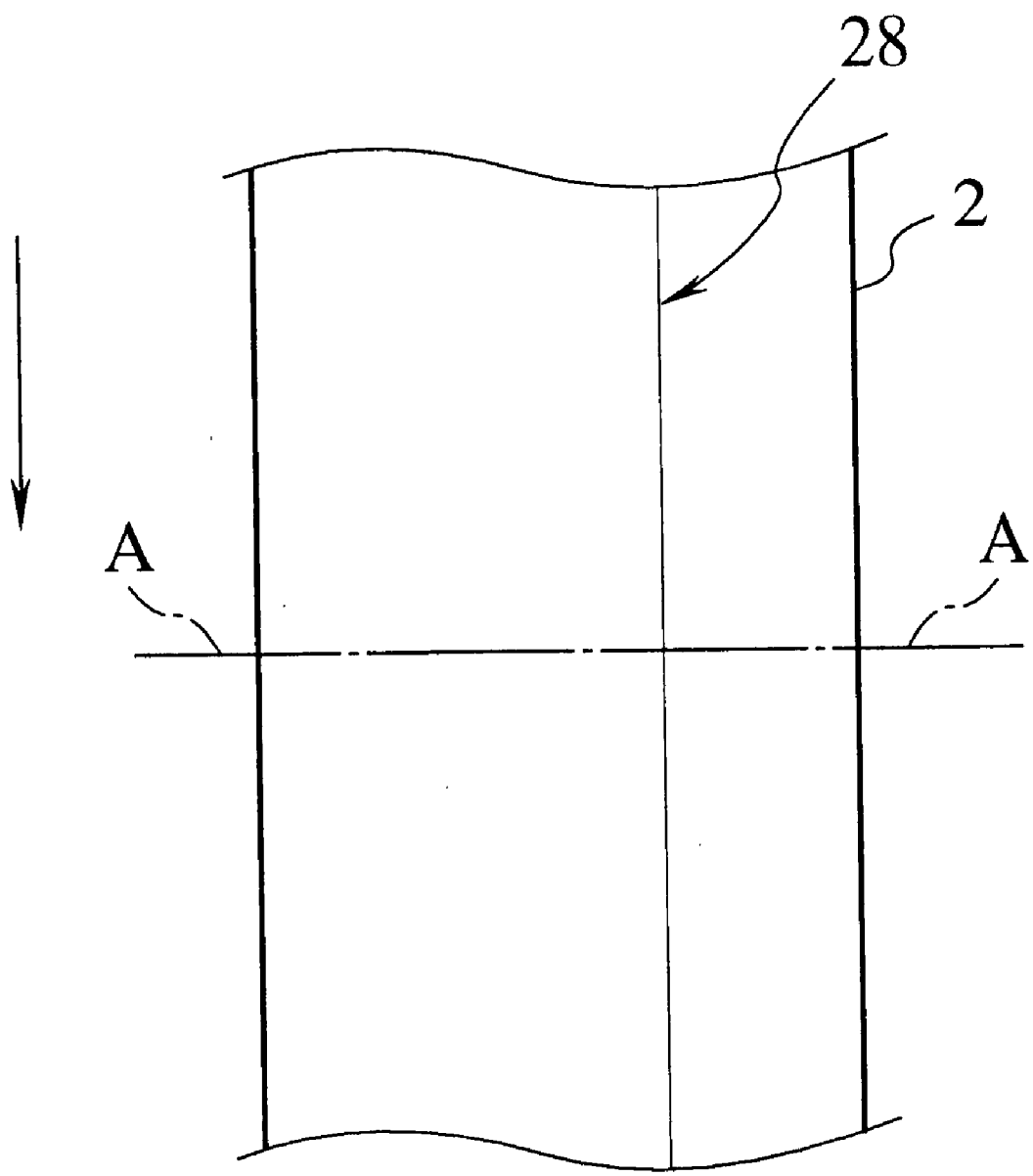
FIG. 2 is an explanatory diagram of a streak on a sheet.

FIG. 2 shows the sheet 2 (FIG. 1) of which an image is being taken by the line sensor camera 3. In FIG. 2, the sheet 2 is transported in the direction of the arrow. Further, it is assumed that a streak 28 to be inspected runs parallel with the transporting direction of the sheet 2, exhibits a fine, long and straight scratch or defect on the sheet 2. According to the invention, even if the streak 28 has a small contrast ratio in comparison with the surroundings, it is possible to detect the streak 28 properly. Note, a line A—A of FIG. 2 designates a portion of the sheet 2 that the line sensor camera 3 takes a picture thereof.

Figure 3A:
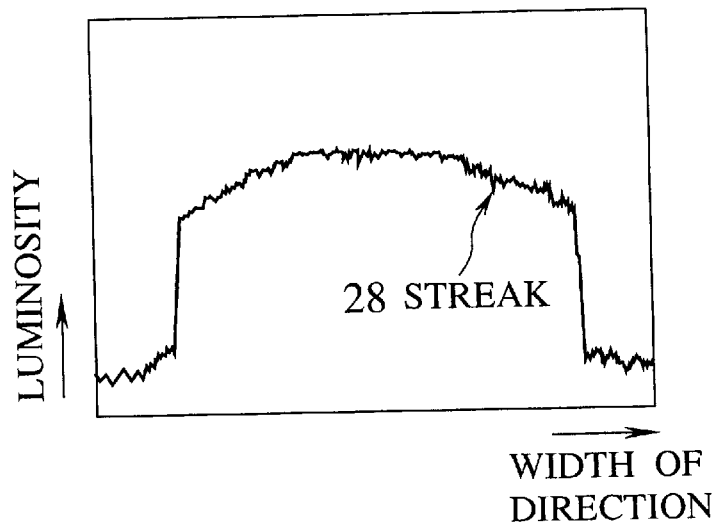
FIGS. 3A and 3B are further explanatory diagrams of the streak on the sheet.

FIG. 3A shows one line of image signals which are obtained by the line sensor camera taking the picture above the line A—A containing the streak 28 and which are input into the inspection control device 11. In FIG. 3A, a horizontal axis represents a width of the sheet 2, while a vertical axis represents luminosity. From the figure, it will be understood that a signal representing the streak 28 is included in the upper part of the signals. However, since the signal representing the streak 28 has small differences in luminosity and width, namely, a difference in contrast, in comparison with the surrounding signals having no streak, it has been difficult to detect the streak 28 even if either of the above-mentioned micro-filtering process or the unevenness filtering process are used.

Figure 3B:
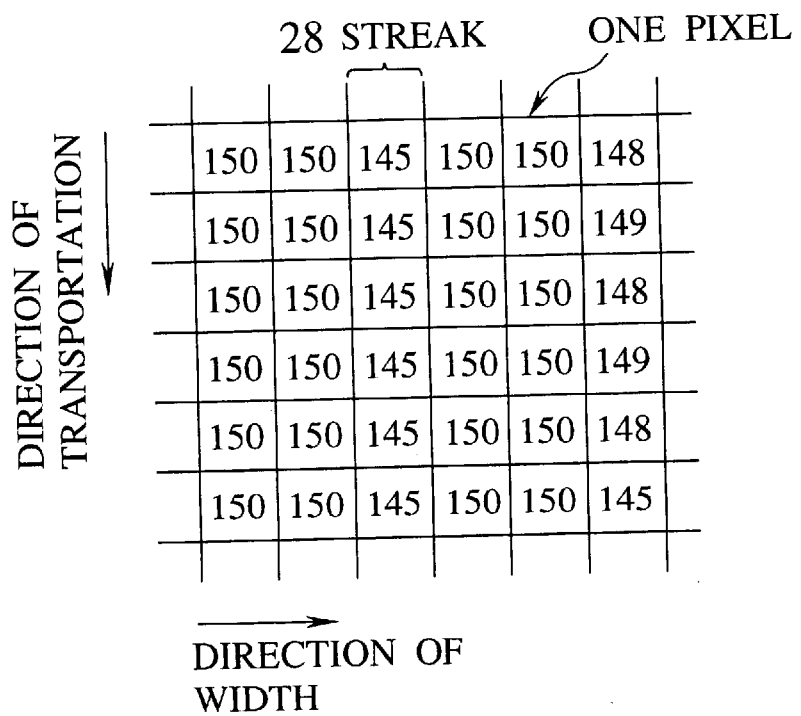

FIG. 3B shows a schematic data structure in which the image signals of FIG. 3A are introduced into the frame memory 24 described later while a picturing line of the camera 3 is shifted one by one together with the transportation of the sheet 2. That is, although the data structure of FIG. 3B is shown in a manner of lattices, each lattice corresponds to one pixel. In this figure, a shown horizontal direction represents a width direction of the sheet 2, while a vertical direction represents a transporting direction along which the sheet 2 is to be transported. Further, numerical data shown in the respective lattices represent degrees of luminosity or darkness. In this embodiment, it is established that the darkest condition can be represented by a numeral of 0 (zero), while the luminous condition can be represented by a numeral of 255. Thus, FIG. 3B is now provided by way of example of the image signals of FIG. 3A, corresponding to the streak 28 of FIG. 2 as an object to be inspected.

From FIG. 3B, it will be noted that numerical data of 145 are stored in a column of the streak 28, while numerical data of 150 are stored in other columns. The column with the numerals data of 145 shows the luminosity of the streak 28, while the circumference of the streak 28 shows a proper area on the sheet 2. In this way, it will be understood that a difference between the luminosity of the streak 28 and the luminosity of the proper area is small in the extreme, exhibiting a so-called "low-contrast" condition.

We now describe the detailed constitution of the inspection control device 11 with reference to FIG. 1. The image input unit 22 comprises an A/D converter, shade correcting means, reflection calculating means and luminosity correcting means etc., all of which are not shown in the figure.

In operation, when the sheet 2 is detected by the sensor 7 so that the encoder 21 outputs pulse signals, the image input unit 22 synchronizes the video signals brought by the line sensor camera 3 with the pulse signals for digitalization. Thereafter, the image data is subjected to the shade correction, the reflection correction and the luminosity correction in the image input unit 22 and finally output therefrom.

Figures 4, 5:
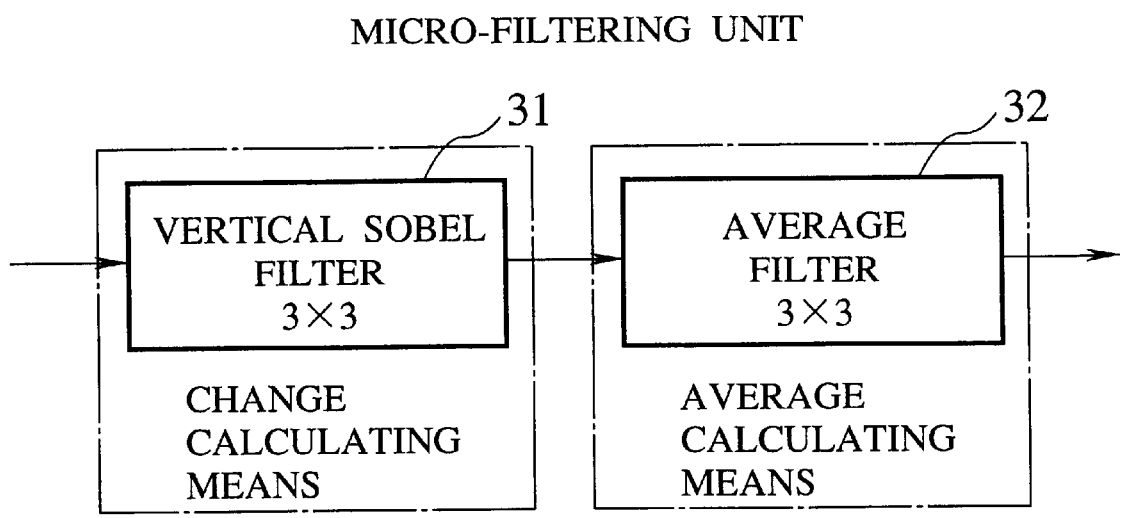
FIG. 4 is a schematic constituent diagram of a micro-filtering unit.
FIG. 5 is an explanatory diagram for explanation of a vertical Sobel filter of the micro-filtering unit of FIG. 4.

The micro-filtering unit 25 comprises a vertical Sobel filter 31 which is constituted by space filters of three rows and three columns for calculation of changes and an average filter 32 for calculating an average of the changes, as shown in FIG. 4.

In this micro-filtering unit 25, owing to the vertical Sobel filter 31, respective vertical and horizontal density changes in nine lattice areas consisting of three rows and three columns are detected. Thereafter, the respective changes are added for every pixel and an average of the added changes is calculated using the average filter 32. The so-calculated average is then employed as representing an average of change of the center pixel in nine lattices of three rows and three columns. In this way, a profile of the streak 28 in the horizontal direction, namely, the width direction of the sheet 2 can be emphasized.

As shown in FIG. 5, the vertical Sobel filter 31 has respective coefficients for emphasis, which have been established for the lattices of three rows and three columns, respectively: −1, −2, −1 in the left column from the upside, in order; 0, 0, 0 in the center column from the upside; and 1, 2, 1 in the right column from the upside.

For example, the horizontal change Hij of an optional pixel Lij is obtained by the vertical Sobel filter 31 (FIG. 5) using the following expression, on the basis of respective density information of nine lattices of three rows and three columns about the center pixel Lij as shown in FIG. 6.

$$Hij=|-L_{i-1, j-1}+L_{i+1, j-1}-2L_{i-1, j}+2L_{i+1, j}-L_{i-1, j+1}+L_{i+1, j+1}| \quad (1)$$

We now describe the above calculation by the vertical Sobel filter 31, taking example of the data structure of FIG. 3B. That is, against the data of three rows and three columns shown with a thick frame in FIG. 7A, a process to calculate a sum of products is applied by making use of the vertical Sobel filter 31. Then, the calculation for the thick frame is successively executed while shifting one pixel at a time from the left to the right. Thereafter, upon sequent shifting one stage below, the calculation is executed from the left to the right again. FIG. 7B shows the image signals of one row 33 in FIG. 7A.

FIGS. 8A and 8B show the calculation results of the sum of products for every nine lattices (pixels). Designated in one lattice in FIG. 8A is the calculation result of the sum of products, which has been carried out for nine pixels in FIG. 7A. From FIG. 8A, it will be understood that the low-contrast data in density value according to the unit of pixel shown in FIGS. 7A and 7B is arranged to emphasize the difference in contrast. FIG. 8B shows the image signals corresponding to the data of one row 34 in FIG. 8A. That is, a negative peak 34a of FIG. 8B is representative of a signal corresponding to a value of −20 of FIG. 8A, while a positive peak 34b is representative of a signal corresponding to a value of 20 of FIG. 8A.

FIGS. 9A and 9B show the absolute values of the data shown in FIGS. 8A and 8B. In the figures, FIG. 9A shows the numerals of the data, while FIG. 9B shows the image signals. In this way, the streak data having low contrast shown in FIGS. 7A and 7B is modified into new data of which feature is emphasized as shown in FIGS. 9A and 9B.

Further, the image data shown in FIG. 9A is averaged by the average filter 32 of FIG. 4. This averaging process is executed by calculating an average of the data of FIG. 9A for every three rows and three columns.

Figure 10:
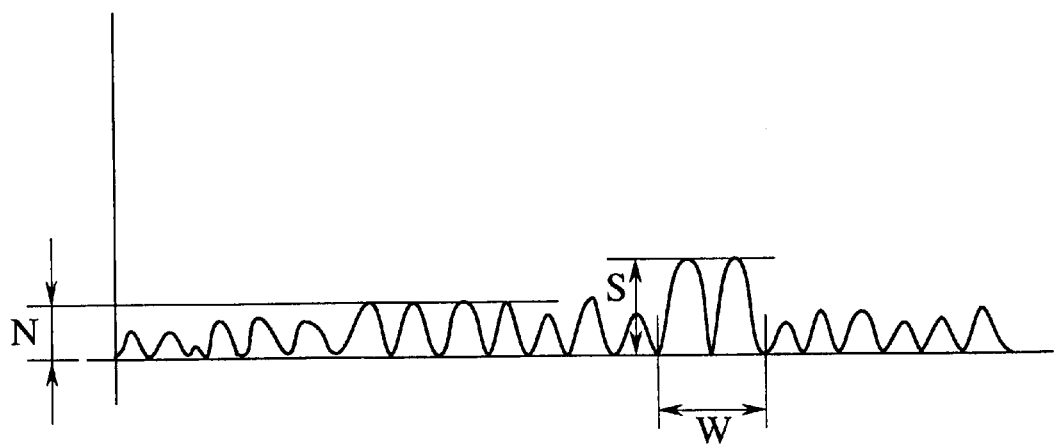
FIG. 10 is an explanatory diagram for explanation of an averaging process executed in the micro-filtering unit.
Figure 11:
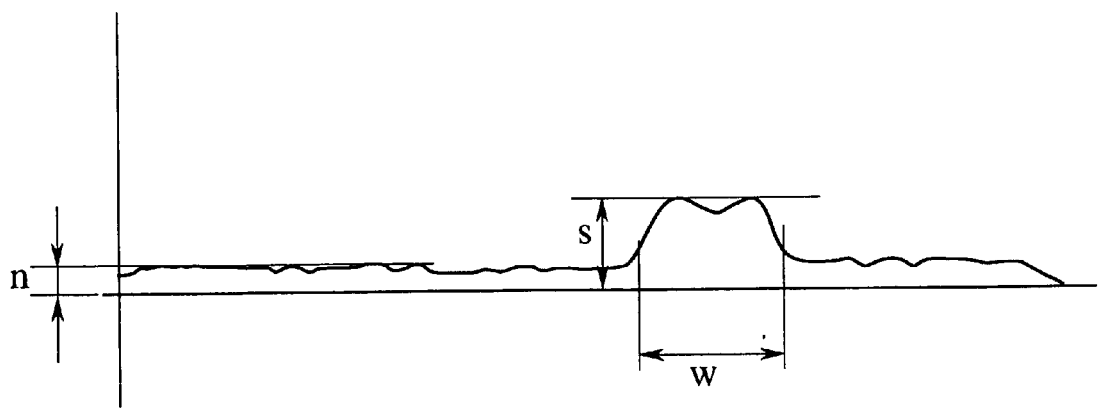
FIG. 11 is an explanatory diagram for explanation of a result of the averaging process in the micro-filtering unit.

FIG. 10 shows the image signals before the above-mentioned averaging process, which are identical to the signals of FIG. 9B. In FIG. 10, a height of signal corresponding to the streak 28 is represented by a letter S, a width of the signal by a letter W and a height of signals surrounding the streak 28 is designated by a letter N. While, FIG. 11 is a diagram showing the image signals after the averaging process, in which a height of signal corresponding to the streak 28, a width of the signal and a height of the signals surrounding the streak 28 are represented by letters s, w and n, respectively. In this way, the streak 28 is further characterized, so that respective relationships of n/N<s/S and W<w are established. Consequently, a width of the signal corresponding to the streak 28 is enlarged in comparison with that of the signal before executing the averaging process. However, it should be noted that, even such a condition, it is impossible to extract the signal representing the streak 28 from the image signals perfectly and precisely.

Now, the present invention comes into effect by the unevenness-filtering process described below.

Figure 12:
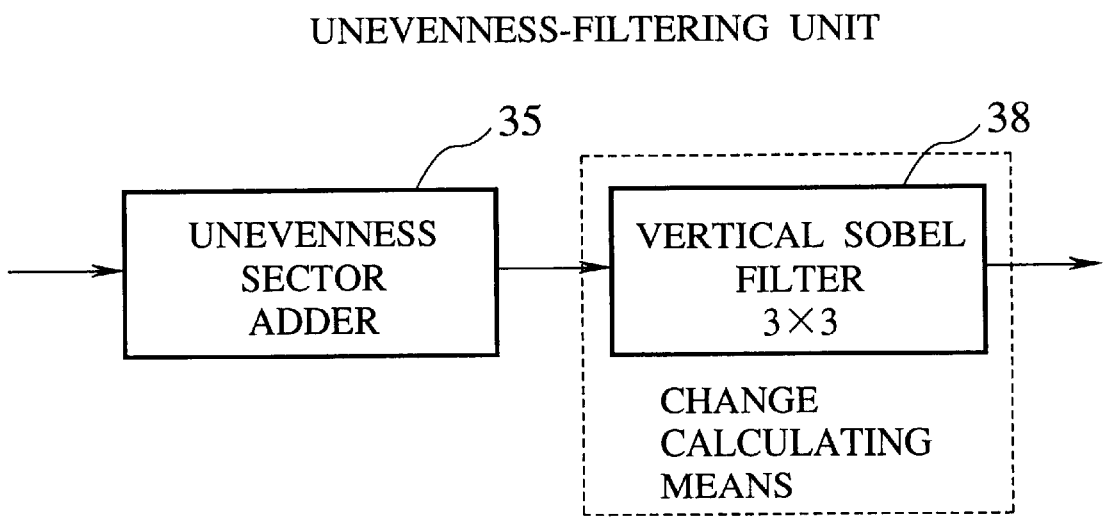
FIG. 12 is a schematic constituent diagram of an unevenness-filtering unit.

The data averaged in the above way is further processed by the unevenness-filtering unit of FIG. 12. The averaged data is stored in respective lattices 36 shown in (a) of FIG. 13. Then, an unevenness sector adder 35 operates to calculate an addition value Σ of the averaged data for every lattices of 6×30 while shifting one calculating section after another calculating section. As a result, lattice data consisting of the addition values Σ can be obtained as shown in (b) of FIG. 13.

In this way, according to the embodiment, the lattice data, which is long (30 lattices) in a direction of the streak's extending and short (6 lattices) in a direction perpendicular to the extending direction of the streak, is employed for extracting the characteristics of the fine, long and straight streak by the unevenness sector adder 35. That is, as shown with the thick frame of FIG. 13, the adding process is executed in blocks of an area longer than it is wide.

Figure 13:
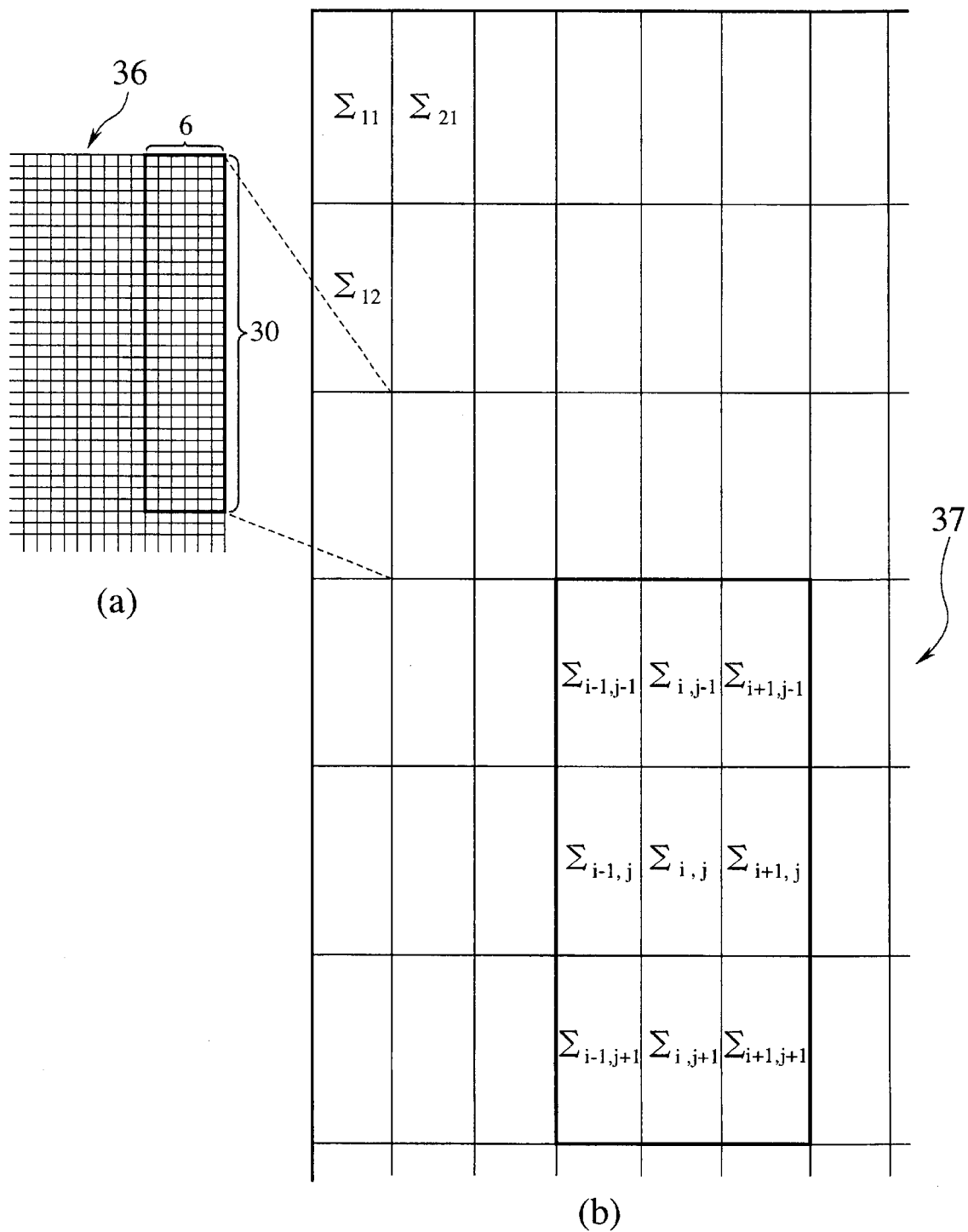
FIG. 13 is an explanatory diagram for calculation of changes in the unevenness-filtering unit.
Figure 14:
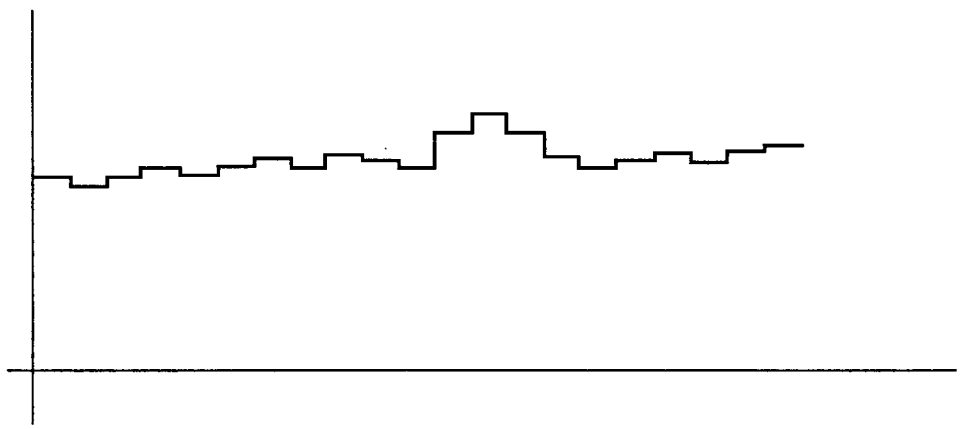
FIG. 14 is an explanatory diagram for calculation of a sum in the unevenness-filtering unit.

FIG. 14 is a diagram showing the image signals corresponding to a row 37 of FIG. 13. Consequently, it can be obtained of a well-modulated signals of FIG. 14, in comparison with gently-sloping signals as shown in FIG. 13.

Thereafter, changes of the addition values Σ are calculated by a vertical Sobel filter 38 of FIG. 12. Note, the vertical Sobel filter 38 is similar to the afore-mentioned vertical Sobel filter 31 of FIG. 15.

For example, the horizontal change Sij of the addition values Σij of an optional lattice is obtained by the vertical Sobel filter 31 (FIG. 5) using the following expression (2), on the basis of respective density addition values of nine lattices of three rows and three columns about the center density addition values Σij as shown in (b) of FIG. 13.

$$Sij=|-\Sigma_{i-1, j-1}+\Sigma_{i-1, j-1}-2\Sigma_{i-1, j}+2\Sigma_{i-1, j}-\Sigma_{i-1, j+1}+\Sigma_{i+1, j+1}| \quad (2)$$

In this way, according to the embodiment, the unevenness is emphasized by dividing the density information in each pixel of the object to be inspected, which can be obtained by the line sensor camera 3, into the meshes consisting of a matrix of several pixels vertically and horizontally and sequent adding the density information in each pixel of the respective meshes thereby calculating the density sum (additional value) of each mesh. In addition, the unevenness is further emphasized by calculating the horizontal change Sij among the respective lattices in the matrix of three rows and three columns.

In other words, by arranging the defect data after the micro-filtering into the lattices and subsequently integrating the defect data along the directions of arrangement by means of the horizontal and vertical Sobel filters, it is possible to obtain the unevenness defect data in an area based on the orientations of streak.

Figure 15:
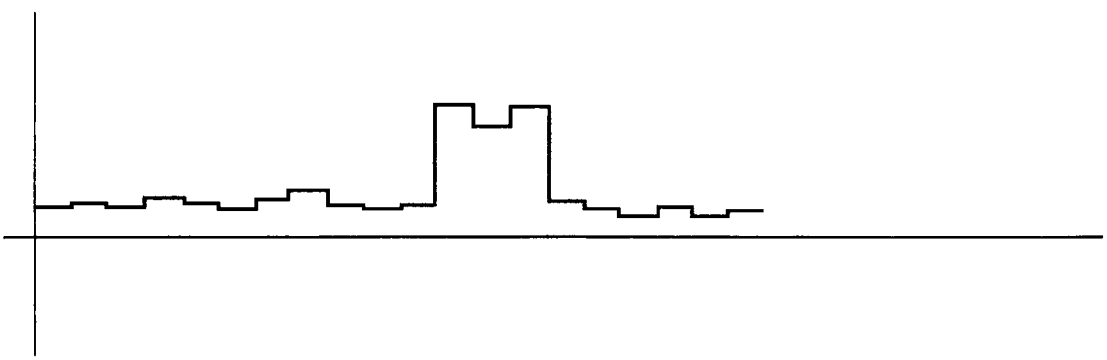
FIG. 15 is an explanatory diagram for calculation of changes of the sum in the unevenness-filtering unit.

Accordingly, against an area of 3×3 shown with the thick frame of (b) of FIG. 13, a process to calculate a sum of products is carried out by the vertical Sobel filter 38. Consequently, it can be obtained of signals in which a portion of streaks is emphasized and each boundary between the portion and the circumference is clarified, as shown in FIG. 15.

Figure 16:
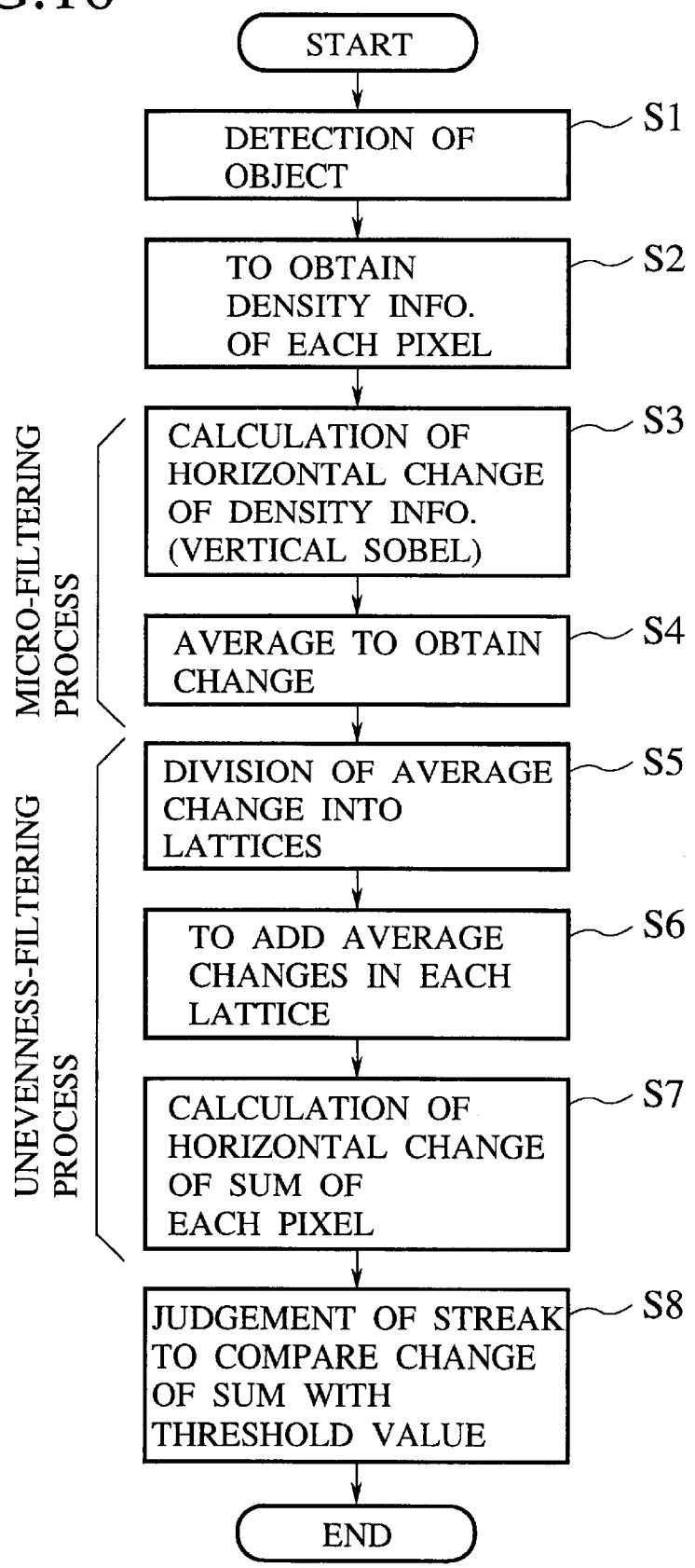
FIG. 16 is an explanatory flow chart in accordance with the streak inspecting method of the present invention.

Now, with reference to FIG. 16, we describe an operation of the streak inspection apparatus constructed in the above-mentioned way.

For instance, if the sheet 2 having the streak 28 of low contrast is transported and when the sheet 2 is detected by the sensor 7, then a detection signal is output from the sensor 7 to the inspection control device 11 (at step S1).

With an input of the detection signal, one line of video signals generated from the line sensor camera 3 are input into the image input unit 22 for digital conversion. Thereafter, the converted signals are subjected to a correction process based on optical errors, so that the image data can be obtained (at step S2). Note, the image data possesses the density information for each pixel.

At step S3, the image data is input into the micro-filtering unit 25 where the change calculating means 31 calculates the horizontal change Hij among the respective density information with respect to the pixels, in the matrix of three rows and three columns.

Next, at sequent step S4, the average filter 32 of the average calculating means calculates an average of nine changes consisting of three rows and three columns as the average change of the center pixel.

Accordingly, owing to the provision of the micro-filtering unit 25, the fine streak with low contrast is so enlarged as to have several bits in width. In other words, after the streak is enlarged to have enough defect-size for the unevenness filtering unit 26 to identify it, the streak is output from the unit 25.

The average changes calculated at the micro-filtering unit 25 are input by the unevenness filtering unit 26 which carries out the following processes.

The unevenness filtering unit 26 receives the micro-defect data from the micro-filtering unit 25 through an unevenness sector adder 35. At step S5, the unevenness sector adder 35 serves to divide the density information of respective pixels into the lattices (i.e. meshes) consisting of a matrix of several pixels vertically and horizontally and add the density information in the respective pixels of each lattice thereby calculating a density sum (additional value) of each mesh (step S6).

Next, the change calculating means 38 of the unevenness filtering unit 26 calculates a horizontal change Sij among the respective lattices in the matrix of three rows and three columns (step S7).

Then, the defect judging unit 27 judges that if a vertical or horizontal length of the unevenness defect data is more than a predetermined length, the streak exists to the same direction (step S8).

Accordingly, owing to the provision of the micro-filtering unit 25 and the unevenness filtering unit 26 connected with the unit 25 in series, even if the line sensor camera 2 detects the microscopic streak with low contrast, it can be effectively emphasized to generate to the defect judging unit 27 where the streak having the predetermined length would be judged as "streak" to be objected.

Finally, it will be understood by those skilled in the art that the foregoing description is one of preferred embodiments of the disclosed method and apparatus, and that various changes and modifications may be made to the present invention without departing from the spirit and scope thereof.

What is claimed is:

1. A streak inspection method of inspecting an existence of a linear streak on a sheet object to be inspected in a transportation direction, by taking a picture of the sheet object to be inspected during transportation to obtain a video signal, and converting the video signal to obtain a plurality of brightness data for every pixel, said streak inspection method comprising:

a first change calculation step of emphasizing density changes in vertical and horizontal directions by applying a first emphasizing filter on the plurality of brightness data for every pixel;

an average calculation step of dividing the density changes emphasized in said change calculation step into a plurality of first lattices composed of a plurality of data, and calculating an average value of the divided data to obtain average changes for every first lattice;

an change addition step of dividing the average changes calculated in said average calculation step into a plurality of second lattices composed of a plurality of rows and columns in a lengthwise and breadthwise direction, and adding the average changes in each second lattice to obtain average change sums for each second lattice;

a second change calculation step of emphasizing the density changes in vertical and horizontal directions by applying a second emphasizing filter on the average change sums obtained in said change addition step; and a defect judgement step of judging a streak by comparing the density changes emphasized in said second change calculation step with a predetermined threshold value.

2. A streak inspection method as claimed in claim 1, wherein said change addition step comprises a step of dividing the plurality of data into the second lattice so that the number of data in the transportation direction is lager than the number of data in a direction perpendicular to the transportation direction, and adding the density changes in the second lattice to obtain the average change sums for each second lattice.

3. A streak inspection apparatus for inspecting an existence of a linear streak on a sheet object to be inspected, said streak inspection apparatus comprising:

a camera for taking a picture of the sheet object to be inspected during transportation;

an image input unit for inputting a plurality of brightness data for each pixel obtained by converting the video signal from the camera;

a micro-filtering unit including:
a first change calculation means for emphasizing density changes in vertical and horizontal directions by applying a first emphasizing filter on the plurality of brightness data from said image input unit; and
an average calculation means for dividing the density changes emphasized in said first change calculation means into a plurality of first lattices composed of a plurality of data, and calculating an average of the divided data to obtain average changes for every first lattice; an unevenness-filtering unit including:
an unevenness sector adder for dividing the average changes calculated in said micro-filtering unit into a plurality of second lattices composed of a plurality of rows and columns in a lengthwise and breadthwise direction, and adding the average changes in the second lattices to obtain average change sums for each second lattice; and
a second change calculation means for emphasizing the density changes in vertical and horizontal directions by applying a second emphasizing filter on the plurality of average change sums obtained in said unevenness sector adder; and a defect judging unit for detecting and judging a streak as a defect by comparing the density changes emphasized in said unevenness-filtering unit with a predetermined threshold value.

4. A streak inspection apparatus as claimed in claim 3, wherein said unevenness sector adder divides the plurality of data into the second lattice so that the number of data in a transportation direction is lager than the number of data in a direction perpendicular to the transportation direction, and adding the density changes in the second lattice to obtain the average change sums for each second lattice.

5. A streak inspection method of inspecting an existence of a linear streak on a sheet object to be inspected in a transportation direction, by taking a picture of the sheet object to be inspected during transportation to obtain a video signal, and converting the video signal to obtain a plurality of brightness data for every pixel, said streak inspection method comprising:

a first change calculation step of emphasizing a difference in contrast in vertical and horizontal directions by applying a first Sobel filter on the plurality of brightness data for every pixel, and obtaining an absolute value of the data emphasized by the first Sobel filter;

an average calculation step of dividing the density changes emphasized in said change calculation step into a plurality of first lattices composed of a plurality of data, and calculating an average value for each first lattice to magnifying data corresponding to a streak;

an change addition step of dividing the average changes calculated in said average calculation step into a plurality of second lattices so that the number of data in the transportation direction is lager than the number of data in a direction perpendicular to the transportation direction, and adding the average changes in each second lattice to obtain average change sums for each second lattice;

a second change calculation step of emphasizing the density changes in vertical and horizontal directions by applying a second Sobel filter on the average change sums obtained in said change addition step, and obtaining an absolute value of the data emphasized by the second Sobel filter; and a defect judgement step of judging a streak by comparing the density changes emphasized in said second change calculation step with a predetermined threshold value.

* * * * *